US008663619B2

(12) United States Patent
Zhang et al.

(10) Patent No.: US 8,663,619 B2
(45) Date of Patent: Mar. 4, 2014

(54) MURGANTIOL AS AN INDOOR STINK BUG ATTRACTANT

(75) Inventors: Qing-He Zhang, Spokane Valley, WA (US); Rodney G. Schneidmiller, Greenacres, WA (US); Guiji Zhou, Spokane, WA (US); Doreen R. Hoover, Spokane, WA (US)

(73) Assignee: Sterling International Inc., Spokane, WA (US)

( * ) Notice: Subject to any disclaimer, the term of this patent is extended or adjusted under 35 U.S.C. 154(b) by 22 days.

(21) Appl. No.: 13/180,281

(22) Filed: Jul. 11, 2011

(65) Prior Publication Data

US 2012/0294828 A1 Nov. 22, 2012

Related U.S. Application Data

(60) Provisional application No. 61/488,069, filed on May 19, 2011.

(51) Int. Cl.
*A01N 43/20* (2006.01)
*A01P 19/00* (2006.01)
*A01M 1/04* (2006.01)

(52) U.S. Cl.
USPC .............................................. 424/84; 43/113

(58) Field of Classification Search
USPC ......................................................... 43/113
See application file for complete search history.

(56) References Cited

U.S. PATENT DOCUMENTS

| | | | |
|---|---|---|---|
| 6,387,933 B1 | 5/2002 | Nakamura | |
| 6,413,508 B1 | 7/2002 | Dickens | |
| 7,150,125 B1 | 12/2006 | Mizell, III | |
| 7,824,668 B2 | 11/2010 | McKibben | |
| 2008/0044375 A1* | 2/2008 | McKibben | 424/84 |
| 2008/0263938 A1 | 10/2008 | Schneidmiller | |
| 2013/0104445 A1 | 5/2013 | Schneidmiller | |

OTHER PUBLICATIONS

Identification, Synthese, and Bioassay of a Male-Specific Aggregation Pheromone from the Harlequin Bug, *Murganti histrionica*. Zahn. et al J. Chem Ecol (2008) 34: 238-251.*
Methyl 2,4,6-decatrienoates Attract Stink bugs and Tachinid Parasitoids. Aldrich et al. J Chem Ecol (2007) 33:801-815.*
Aldrich et al., Semiochemically based monitoring of the invasion od the brown marmorated stink bug and unexpected attraction of the native green stink bug in Maryland, Florida Entomologist, 2009, vol. 92, pp. 483-491.*
Gill, The brown mamorated stink bug, Growertalks, Pest Management, 2010, http://www.ballpublish.com/growertalks/viewarticle.aspx?articleid=18206.*
Aldrich, J.R., et al., "Identification and Attractiveness of a Major Pheromone Component for Nearctic *Euschistus* spp. Stink Bugs (Heteroptera: Pentatomidae)," Environ. Entomol. 20(2):477-483, Apr. 1991.

Aldrich, J.R., et al., "Methyl 2,4,6-decatrienoates Attract Stink Bugs and Tachinid Parasitoids," J. Chem. Ecol. 33(4):801-815, Apr. 2007.
Gill, S., et al., "Brown Marmorated Stink Bug (*Halyomorpha halys*)," IPM Pest Alert, University of Maryland Extension, Oct. 2010, 4 pages.
Gill, S., et al., "The Brown Marmorated Stink Bug (*Halyomorpha halys*)," IPM Garden Center Fact Sheet, University of Maryland Extension, Mar. 2011, 4 pages.
Khrimian, A., "The Geometric Isomers of Methyl-2,4,6-decatrienoate, Including Pheromones of at Least Two Species of Stink Bugs," Tetrahedron 61(15):3651-3657, Apr. 2005.
McBrien, H.L., et al., "Sex Attractant Pheromone of the Red-Shouldered Stink Bug *Thyanta pallidovirens*: A Pheromone Blend With Multiple Redundant Components," Journal of Chemical Ecology 28(9):1797-1818, Sep. 2002.
Millar, J.G., "Methyl (2E,4Z,6Z)-Deca-2,4,6-trienoate, a Thermally Unstable, Sex-Specific Compound From the Stink Bug *Thyanta pallidovirens*," Tetrahedron Letters 38(46):7971-7972, Nov. 1997.
Millar, J.G., et al., "Pentatomid Bug Pheromones in IPM: Possible Applications and Limitations," in P. Witzgall et al. (eds.), Pheromones and Other Biological Techniques for Insect Control in Orchards and Vineyards: Proceedings of the Working Group Meeting, Samos, Greece, Sep. 25-29, 2000, IOBC WPRS Bulletin 25(9), 2002, 11 pages.
Moraes, M.C.B., et al., "Sex Attractant Pheromone From the Neotropical Red-Shouldered Stink Bug, *Thyanta perditor* (F.)," Journal of Chemical Ecology, 31(6):1415-1427, Jun. 2005.
Sugie, H., et al., "Identification of the Aggregation Pheromone of the Brown-Winged Green Bug, *Plautia stali* Scott (Heteroptera: Pentatomidae)," Appl. Entomol. Zool. 31(3):427-431, 1996.
Zahn, D.K., et al., "Identification, Synthesis, and Bioassay of a Male-Specific Aggregation Pheromone From the Harlequin Bug, *Murgantia histrionica*," J Chem Ecol 34(2):238-251, Feb. 2008.
Zhang, Q-H., et al., "Murgantiol as a Stink Bug Synergistic Attractant for use Outdoors," U.S. Appl. No. 13/410,124, filed Mar. 1, 2012.
Lacey, E.S., et al., "Male-Produced Aggregation Pheromones of the Cerambycid Beetles *Xylotrechus colonus* and *Sarosesthes fulminans*," Journal of Chemical Ecology 35(6):733-740, Jun. 2009.
International Search Report and Written Opinion mailed Jan. 28, 2013, issued in corresponding International Application No. PCT/US2012/029124, filed Mar. 14, 2012, 9 pages.
Endo, N., et al., "Pheromonal Cross-Attraction in True Bugs (Heteroptera): Attraction of *Piezodorus hybneri* (Pentatomidae) to Its Pheromone Versus the Pheromone of *Riptortus pedestris* (Alydidae)," Environmental Entomology 39(6):1973-1979, Dec. 2010.
Millar, J.G., et al., "Field Trials of Aggregation Pheromones for the Stink Bugs *Chlorochroa uhleri* and *Chlorochroa sayi* (Hemiptera: Pentatomidae)," Journal of Economic Entomology 103(5):1603-1612, Oct. 2010.

(Continued)

*Primary Examiner* — Kevin S Orwig
*Assistant Examiner* — Ping Cao
(74) *Attorney, Agent, or Firm* — Christensen O'Connor Johnson Kindness PLLC (57) ABSTRACT

Provided herein are uses of murgantiol for attracting stink bugs in indoor settings. Stink bug traps comprising murgantiol and methods of using murgantiol in traps indoors are provided. Compositions comprising murgantiol are also described.

12 Claims, 3 Drawing Sheets

(56) References Cited

OTHER PUBLICATIONS

Tillman, P.G., et al., "Pheromone Attraction and Cross-Attraction of *Nezara, Acrosternum*, and *Euschistus* spp. Stink Bugs (Heteroptera: Pentatomidae) in the Field," Environmental Entomology 39(2):610-617, Apr. 2010.

Zahn, D.K., et al., "Identification, Synthesis, and Bioassay of a Male-Specific Aggregation Pheromone From the Harlequin Bug, *Murgantia histrionica*," Journal of Chemical Ecology 34(2):238-251, Feb. 2008.

Prosecution history of U.S. Appl. No. 13/410,124, filed Mar. 1, 2012.

\* cited by examiner

MURGANTIOL AS AN INDOOR STINK BUG ATTRACTANT

CROSS-REFERENCE TO RELATED APPLICATION

This application claims the benefit of U.S. Provisional Application No. 61/488,069, filed May 19, 2011, which is incorporated herein by reference in its entirety.

BACKGROUND

Pesticides, such as insecticides, are commonly used in agricultural, industrial, and residential settings to battle destructive, pestiferous, or disease-carrying insects and other animals. Pesticides have achieved significant successes in controlling pestiferous and disease-vector animals, and have increased in their lethality over the years. However, increasingly the environmental and human health effects of pesticides, as well as their deleterious effects on beneficial insect species and other animals, have caused users to seek other means for controlling pest populations.

For example, many stink bugs and shield bugs (order Hemiptera; family Pentatomidae) are considered agricultural pest insects, although some are beneficial insects. Examples include the spined soldier bug, *Podisus maculiventris*, several species of *Euschistus* spp., the red-shouldered stink bug, *Thyanta pallidovirens*, the green stink bug, *Acrosternum hilare*, the conchuela stink bug, *Chlorochroa ligata*, Uhler's stink bug, *C. uhleri*, and Say's stink bug, *C. sayi*, Some can generate large populations that damage crop production and are resistant to many pesticides. Moreover, they are immune to genetically modified crops, such as Bt crops. Over the past 5-10 years, stink bugs and plant bugs have become a serious agricultural pest problem in many parts of the world, especially in the regions with large areas of Bt crops.

As an example, the brown marmorated stink bug (BMSB), *Halyomorpha halys* (Stål) native to Asia, is believed to have been accidentally introduced into the United States as early as 1996, likely as a collection of stowaways, possibly as eggs, on packing crates or the like. The BMSB has been recorded in a total of 33 states and the District of Columbia, according to information provided by the U.S. Department of Agriculture and the National Pest Management Association. In 2010, the BMSB emerged as a severe pest of fruit and other crops across the region. In addition, this invasive species is a serious nuisance for homeowners and businesses as it overwinters in residential houses, commercial buildings, and warehouses.

Aggregation pheromone components have been identified from many species of agriculturally important stink bugs. In 2008, Zahn et al. noted that for all phytophagous pentatomids for which sex or aggregation pheromones have been identified, the compounds were produced by males. *J. Chem. Ecol.* 34:238 (2008). Males of *Thyanta* spp., for example, produce methyl (2E,4Z,6Z)-decatrienoate with (Millar, *Tetrahedron Lett.* 38:7971 (1997); McBrien et al., *J. Chem. Ecol.* 28:1797 (2002)) or without particular sesquiterpenes (Moraes et al., *J. Chem. Ecol.* 31:1415 (2005)) that attract a mate. J. G. Millar et al. reported findings regarding male-produced pheromone components of several agriculturally important stink bugs, including *T. pallidovirens*, *A. hilare*, *C. sayi*, *C. uhleri*, and *C. ligata*. *Bull. Int. Org. of Biol. Control*, Pheromone Working Group 25:1 (2002). Methyl 2E,4Z-decadienoate has been identified as an aggregation pheromone component or field attractant for seven *Euschistus* spp. (Aldrich et al., *Environ. Entomol.* 20:477 (1991)), and has been used for stink bug monitoring programs in agricultural settings. Another methyl ester, methyl 2E,4E,6Z-decatrienoate, was identified as an aggregation pheromone component of the stink bug *Plautia stali* Scott (Sugie et al., *Appl. Entomol.* 31:427 (1996)) and as a field attractant for both adults (males and females) and nymphs of the BMSB, *Halyomorpha halys* (Stål) and *A. hilare* (Aldrich et al., *J. Chem. Ecol.* 33:801 (2007)); Khrimian, *Tetrahedron* 61:3651 (2005)). Recently, a sesquiterpene epoxyalcohol, murgantiol, was identified by Zahn et al., *J. Chem. Ecol.* 34:238 (2008), as an aggregation pheromone component of the Harlequin bug, *Murgantia histrionica* (Hahn).

Among the economically important phytophagous pentatomid stink bugs, some of them, such as the BMSB and the boxelder bug, *Boisea trivittata* (Say), are also serious nuisances for homeowners and businesses as they overwinter in residential houses, commercial buildings, and warehouses.

Attractant-baited stink bug traps are effective for trapping various stink bugs outdoors. However, when the stink bugs begin to overwinter and go indoors when the weather cools in late fall, they may no longer be attracted by any known pheromone attractant (active during the summer) in the traps. Unfortunately, there are no known semiochemical attractants that are active for these nuisance stink bugs indoors during their overwintering period. Methods and compounds for attracting stink bugs, such as attracting them to traps, are still needed to control these pests.

SUMMARY

In order to develop an efficient stink bug trapping system for stink bugs in indoor settings, the present inventors have recently invented a powerful light trap for stink bugs. At the same time, the present inventors also tested several known stink bug aggregation pheromone compounds, including murgantiol (the Harlequin bug pheromone) on the BMSB during the winter and early-late spring seasons indoors. Based on the results, disclosed herein is a method for attracting a stink bug to an indoor predetermined location, comprising administering to the indoor predetermined location a composition comprising an effective amount of murgantiol, wherein murgantiol is active in attracting the stink bug to the indoor predetermined location. Further provided is a trap for attracting and trapping a stink bug, the trap comprising an effective amount of a composition comprising murgantiol, wherein the trap is indoors. Also provided is a method of attracting a stink bug to a stink bug trap, wherein the stink bug trap comprises a plurality of lighting elements (e.g., light-emitting diodes, LEDs), wherein the method comprises exposing a stink bug to an effective amount of murgantiol comprised in a composition disposed within the trap, wherein light from the lighting elements and the murgantiol both attract the stink bug to the stink bug trap, and wherein the stink bug trap is indoors. In some embodiments, a method of attracting stink bugs to a stink bug trap is provided, wherein the stink bug trap comprises a plurality of lighting elements (e.g., LEDs), wherein the method may comprise exposing a stink bug to a synergistic amount or an additive amount of murgantiol comprised in a composition disposed within the trap, wherein light from the lighting elements and the murgantiol synergistically or additively attract the stink bug to the stink bug trap, and wherein the stink bug trap is indoors.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Many attractant-baited stink bug traps are effective for trapping various stink bugs outdoors. However, as the overwintering period begins and the behavior of stink bugs changes as the weather cools in late fall (e.g., go indoors), they may no longer be attracted by any known pheromone attractant (active during the summer) in the traps. Unfortunately, there are no known semiochemical attractants that are active for these nuisance stink bugs during their indoor period.

Stink bugs are often found indoors during the overwintering period of the stink bug. The overwintering period (used interchangeably with "overwintering season" herein) generally relates to a drop in temperatures as winter approaches. Stink bugs will seek warmth, usually found indoors. During the overwintering period, stink bugs are generally less active and normally aggregate in dark spaces for hibernation; however, some of stink bugs may awaken and crawl/walk around in rooms or other indoor spaces when indoor temperatures are high. Such indoor activity creates various inconvenient issues (such as unpleasant smells and other annoying activities) for inhabitants.

Stink bugs may also be found indoors during transition periods that may be referred to as the outdoor-indoor (late fall) and indoor-outdoor (early-late spring) periods that are adjacent to the overwintering period. In the former, stink bugs are beginning to enter the overwintering period and move indoors as temperatures decrease outdoors, or in response to changing day lengths or other environmental stimuli; in the latter, stink bugs are beginning to exit the indoors as temperatures increase outdoors, or in response to changing day lengths or other environmental stimuli. Stink bugs are often seen inside homes and buildings during these periods.

It was generally believed that stink bugs would not respond well to pheromone cues indoors (e.g., during the overwintering or transition periods). Thus, the trapping of stink bugs indoors with semiochemicals during the overwintering or transition periods was thought to be difficult.

Recently, a sesquiterpene epoxyalcohol, murgantiol, was identified as an aggregation pheromone component of the Harlequin bug, *Murgantia histrionica* (Hahn) (Zahn et al, *J. Chem. Ecol.* 34:238 (2008)). As reported by Zahn et al, sexually mature male Harlequin bugs produce a sex-specific compound, identified as one of the stereoisomers of the sesquiterpene epoxyalcohol 4-[3-(3,3-dimethyloxiran-2-yl)-1-methylpropyl]-1-methylcyclohex-2-en-1-ol (murgantiol). In laboratory bioassays by Zahn et al., insect-produced and synthetic murgantiol attracted sexually mature Harlequin bugs of both sexes, suggesting that murgantiol is a male-produced aggregation pheromone, analogous to those found in a number of other phytophagous bug species. However, no data has yet been reported on potential behavioral activity (attraction) of this compound on Harlequin bugs or other stink bugs in the field or during the indoor hibernation aggregation stage.

Using the recently developed Rescue!® Stink Bug Traps (see below for patent application details), the present inventors have discovered that murgantiol, the reported pheromone for the Harlequin bug, is strongly attractive to both sexes of the brown marmorated stink bug (BMSB) adults indoors during the overwintering and transition periods. This is the first indoor attractant useful for any stink bug during the overwintering or transition periods. It is not known if the murgantiol is produced by the BMSB males as part of its aggregation pheromone system or not. In some embodiments, murgantiol may synergize the attraction of BMSB to an LED or other type of light trap indoors. Accordingly, provided herein are methods of employing murgantiol as a stink bug attractant and stink bug traps comprising murgantiol.

Also provided herein is a method for attracting a stink bug to an indoor predetermined location, comprising administering to the indoor predetermined location a composition comprising an effective amount of murgantiol, wherein murgantiol is active in attracting the stink bug to the indoor predetermined location. In some embodiments, the only stink bug attractant employed is murgantiol. In some embodiments, the stink bug is the brown marmorated stink bug. Other stink bugs are described herein. A composition may further comprise methyl (2E,4E,6Z)-decatrienoate, its related stereoisomers, or a combination thereof. The predetermined location may be a stink bug trap (e.g., an indoor stink bug trap). A stink bug trap may comprise a plurality of lighting elements, such as light emitting diodes (LEDs). Stink bug traps are further described herein. The composition may be comprised in a device or dispenser that controllably releases the composition. A composition may further comprise methyl (2E,4E, 6Z)-decatrienoate, its related stereoisomers, or a combination thereof. A composition may further comprise antioxidant or an oil, or a combination thereof, as described herein.

Further provided is a method of attracting a stink bug to a stink bug trap, wherein the stink bug trap comprises a plurality of lighting elements, such as LEDs, the method comprising exposing a stink bug to a synergistic amount of murgantiol comprised in a composition disposed within the trap, wherein the light from the lighting elements and the murgantiol synergistically attract the stink bug to the stink bug trap, and wherein the stink bug trap is indoors. As used herein, a "synergistic amount" refers to an amount that produces greater than additive effects. In some embodiments, the only stink bug attractants are murgantiol and light. In some embodiments, the stink bug is a male or female adult brown marmorated stink bug. Other stink bugs are described herein. A method may further comprise placing the trap indoors.

Also provided is a trap for attracting and trapping a stink bug, the trap comprising an effective amount of a composition comprising murgantiol, wherein the trap is indoors. A trap may be further defined as a brown marmorated stink bug trap. A trap may further comprise a plurality of lighting elements (e.g., LEDs). Traps are further described herein. A trap may comprise a composition that further comprises methyl (2E, 4E,6Z)-decatrienoate, its related stereoisomers, or a combination thereof. A composition may further comprise antioxidant or an oil, or a combination thereof, as described herein. A trap may be further configured to trap a brown marmorated stink bug.

Murgantiol may be obtained synthetically as described by Zahn et al., *J. Chem. Ecol.* 34:238 (2008). Murgantiol is a compound with four chiral centers and 16 possible stereoisomers. The relative and absolute configurations of the insect-produced compound were not identified by Zahn et al. and are presently unknown, but the structure was reported as follows, with carbon numbering shown:

As used herein, "murgantiol" refers to any compound or mixture of compounds (isomers) that exhibits the murgantiol skeleton structure noted above. Thus, murgantiol may refer to a single isomer, a mixture of all 16 isomers, or a mixture of some of these isomers (e.g., a mixture of 2, 3, 4, 5, 6, 7, 8, 9, 10, 11, 12, 13, 14, or 15 isomers, or a mixture of at most or at least 2, 3, 4, 5, 6, 7, 8, 9, 10, 11, 12, 13, 14, or 15 isomers). A mixture may comprise a racemic mixture. A mixture may, for example, entail a mixture of more polar isomers, such as the 4R/S-isomers (4R/S-1S-7S-10S-isomer, 4R/S-1R-7S-10S-isomer, 4R/S-1R-7R-10S-isomer, 4R/S-1R-7R-10R-isomer, 4R/S-1S-7R-10R-isomer, 4R/S-1S-7R-10S-isomer, 4R/S-1S-7S-R-isomer, and the 4R/S-1R-7S-10R-isomer). A mixture may, for example, entail a mixture of less polar isomers, such as the 4S/R-isomers (4S/R-1S-7S-10S-isomer, 4S/R-1R-7S-10S-isomer, 4S/R-1R-7R-10S-isomer, 4S/R-1R-7R-10R-isomer, 4S/R-1S-7R-10R-isomer, 4S/R-1S-7R-10S-isomer, 4S/R-1S-7S-10R-isomer, and the 4S/R-1R-7S-10R-isomer). Some mixtures may entail four isomers, such as the 4R/S-7R/S-isomers (4R/S-7R/S-1R-10R-isomer, 4R/S-7R/S-1R-10S-isomer, 4R/S-7R/S-1S-10S-isomer, and the 4R/S-7R/S-1S-10R-isomer); the 4R/S-7S/R-isomers (4R/S-7S/R-1R-10R-isomer, 4R/S-7S/R-1R-10S-isomer, 4R/S-7S/R-1S-10S-isomer, and the 4R/S-7S/R-1S-10R-isomer); the 4S/R-7R/S-isomers (4S/R-7R/S-1R-10R-isomer, 4S/R-7R/S-1R-10S-isomer, 4S/R-7R/S-1S-10S-isomer, and the 4S/R-7R/S-1S-10R-isomer); and the 4S/R-7S/R-isomers (4S/R-7S/R-1R-10R-isomer, 4S/R-7S/R-1R-10S-isomer, 4S/R-7S/R-1S-10S-isomer, and the 4S/R-7S/R-1S-10R-isomer). In some embodiments, murgantiol is further defined as a mixture of diastereomers of 4-[3S-(3,3-dimethyloxiran-2-yl)-1-methylpropyl]-1-methylcyclohex-2-en-1-ol. In some embodiments, murgantiol is further defined as a mixture of diastereomers of 4-[3R-(3,3-dimethyloxiran-2-yl)-1-methylpropyl]-1-methylcyclohex-2-en-1-ol.

In some embodiments, a composition comprises an isolated mixture defined as a more polar mixture of murgantiol stereoisomers obtained and separated from a racemic mixture, such as a more polar mixture of murgantiol stereoisomers (4R/S-isomers). In some embodiments, a composition comprises an isolated mixture defined as a less polar mixture of murgantiol stereoisomers obtained and separated from a racemic mixture, such as a less polar mixture of murgantiol stereoisomers (4S/R-isomers). The "more polar mixture" and the "less polar mixture" can be easily obtained and separated from a racemic mixture of murgantiol by flash chromatography on silica gel, eluting with 10% ethyl acetate in hexane, with the first fraction being the less polar murgantiol mixture and the later eluting fraction being the more polar murgantiol mixture. Each fraction consists of 8 isomers that are inseparable by the flash chromatography. In some embodiments, a composition comprises a racemic mixture of murgantiol stereoisomers (all 16 stereoisomers).

As used herein, an "effective amount" of murgantiol is an amount effective to achieve a desired result, such as to attract a stink bug to an indoor predetermined location, such as a trap that is indoors. The amount of murgantiol that is used alone or in a composition may be determined experimentally, but ranges of 0.1 to 100 mg may be suitable. For example, 0.1, 10, 20, 30, 40, 50 60, 70, 80, 90, or 100 mg of murgantiol may be employed, or any range derivable therein. Murgantiol may be used alone or in a composition, such as in a composition further comprising one or more semiochemicals, oils, antioxidants, or other additives, or any combination thereof.

Various additives may be combined with murgantiol in compositions, such as those described in U.S. Provisional Appl. No. 61/482,023, filed May 3, 2011, which is incorporated herein by reference. Some of these additives are described below.

Suitable antioxidants for use with murgantiol or murgantiol-containing compositions include, but are not limited to tocopherols, α-tocopherol, ascorbic acid, as well as synthetic antioxidants such as propyl gallate, tertiary butylhydroquinone, butylated hydroxytoluene (BHT), and butylated hydroxyanisole (BHA). BHT or BHA, among other similar antioxidant compounds, are soluble in most of the insect semiochemicals, especially pheromones; and can react efficiently with oxygen in the dispensing systems, therefore avoid oxidation, breakdown, and polymerization of the murgantiol or murgantiol-containing compositions. One class of antioxidants are lipophilic (fat-soluble) organic compounds that are primarily used as antioxidant food additives.

Suitable antioxidants also include polar antioxidants, such as phenolic alcohols, flavonoids, catechins, anthocyanins, and their glycosides. The polar phenolics are advantageous for stabilization of the polar semiochemicals.

While representative oxidants have been listed for purposes of illustrating embodiments of the invention, it is to be appreciated that other antioxidants not specifically listed above may also be used.

Suitable oils to use with murgantiol or murgantiol-containing compositions include, but are not limited to oils derived from plants, such as vegetable oils and nut oils. These are widely available and cost effective. Suitable oils include, but are not limited to canola oil, cottonseed oil, palm oil, safflower oil, soybean oil, corn oil, olive oil, peanut oil, sunflower oil, sesame oil, and coconut oils among many others. Nut oils include, but are not limited to almond oil, cashew oil, hazelnut oil, *macadamia* oil, mongongo nut oil, pecan oil, pine nut oil, pistachio oil, sacha inchi oil, and walnut oil, plus many others. Melon and gourd seed oils are very common and inexpensive. The oils listed above include saturated, monounsaturated, and polyunsaturated fatty acids that are soluble in many insect semiochemicals, especially the less or non-polar ones.

While representative oils have been listed for purposes of illustrating embodiments of the invention, it is to be appreciated that other oils not specifically listed above may also be used.

The oils and antioxidants can be combined with murgantiol for stabilizing murgantiol against oxidation, or for controlling the release rate of murgantiol from a dispenser.

Additional semiochemicals that may be included in a composition with murgantiol include methyl (2E,4E,6Z)-decatrienoate, methyl (2E,4Z,6Z)-decatrienoate, methyl (2E,4E,6E)-decatrienoate, methyl (2Z,4E,6Z)-decatrienoate, or other stereo-isomers; methyl (2E,4Z)-decadienoate; ethyl (2E,4Z)-decadienoate; methyl (2Z,4E)-decadienoate; and methyl (2E,4E)-decadienoate; or any combination thereof.

As used herein, "stink bugs" are insects of the Pentatomoidea family, which include stink bugs, chest bugs, and shield bugs. Any one or more of these stink bugs disclosed herein may be attracted with murgantiol or a murgantiol-containing composition. A variety of stink bugs are known in the art. Non-limiting examples of stink bugs include green stink bug (*Acrosternum hilare* (Say)); several species of *Euschistus* spp. such as the brown stink bug (*Euschistus servus* (Say)), *E. tristigmus*, *E. conspersus*, *E. variolarius*, *E. politus*, or *E. heros*; southern green stink bug (*Nezara viridula* (L.)); eastern green stink bug (*Nezara antennata*); spined soldier bug (*Podisus maculiventris*); East Asian stink bug or yellow-brown stink bug (*Halyomorpha halys*); red-shouldered stink bug (*Thyanta pallidovirens*); globular stink bug (*Megacopta punctatissimum*); white-spotted stink bug (*Eysarcoris ventralis*); fruit-piercing stink bug (*Glaucias subpunctatus*); red-striped stink bug (*Graphosoma rubrolineatum*); brown marmorated stink bug (*Halyomorpha mista*); rice stink bugs (*Lagynotomus elongates, Oebalus pugnax*); two-spotted stink bug (*Perillus bioculatus*); conchuela stink bug (*Chlorochroa ligata*); Uhler's stink bug (*Chlorochroa uhlerii*); Say's stink bug (*Chlorochroa sayi*); brown-winged green stink bug (*Plautia stali* (Scott)); boxelder bug (*Boisea trivittata* (Say)); *Banasa dimidiata* (Say); *B. calva* (Say); *B. euchlora* Stål; and Harlequin bug (*Murgantia histrionica*).

Murgantiol or a murgantiol-containing composition may be used to attract both sexes of adult stink bugs, whether male or female. In some embodiments, a stink bug is a male stink bug. In some embodiments, a stink bug is a female stink bug. In some embodiments, a stink bug is not a male stink bug. In some embodiments, a stink bug is not a female stink bug. In some embodiments, a stink bug is an adult stink bug.

In some embodiments, the stink bug is the brown marmorated stink bug (BMSB). As discussed herein, the BMSB can cause widespread damage to fruit and vegetable crops including peaches, apples, green beans, soybeans, cherries, raspberries, and pears. It is a sucking insect that uses its proboscis to pierce the host plant in order to feed. This feeding may cause necrotic areas on the outer surface of fruits, leaf stippling, cat-facing on tree fruits, seed loss, and transmission of plant pathogens. Frequently, BMSBs survive the winter as adults by entering structures that shield them from the elements. Initially, they may go inside a structure, such as a house, to hibernate but then become more animated due to the warmth of the structure. Adults typically begin overwintering at the end of September or early October and become a nuisance as large numbers congregate and invade buildings in search of overwintering sites.

Murgantiol may be disposed in any trap suitable for stink bug trapping indoors. Indoors includes, but is not limited to, residential houses, residential buildings, office buildings, places of commerce, hotels, warehouses, rural buildings, greenhouses, and the like. It is to be understood that from the first time a stink bug appears indoors that embodiments described herein (e.g., methods and traps) may be employed to attract or trap such a stink bug. It is known that the BMSB may be particularly attracted to green or blue, or other dark colors; this information may be exploited when using stink bug traps. In some embodiments, the trap includes one or more dispensers for holding and releasing murgantiol. Murgantiol may be used, for example, in a stand-alone stink bug trap or in combination with a trap comprising a plurality of lighting elements, such as light emitting diodes (LED). The plurality of lighting elements may be selected to emit light having a wavelength that is targeted specifically to stink bugs.

In some embodiments, an LED may emit light having a wavelength between 380-495 nm. A trap may comprise one or more fluorescent lights, one or more sticky substrates, or one or more colored surfaces for attracting stink bugs. In some embodiments, a trap may not have other kinds of trapping mechanisms. Non-limiting examples of known stink bug traps are described in U.S. Provisional Appl. No. 61/435,647, filed Jan. 24, 2011, U.S. Provisional Appl. No. 61/477,044, filed Apr. 19, 2011, and U.S. Pat. No. 7,150,125, as well as Florida traps (see e.g., Mizell and Tedders, *Proc. Southeast Pecan Growers Assoc.* 90:52 (1990)), wherein each reference is incorporated by reference in its entirety.

Figure 1:
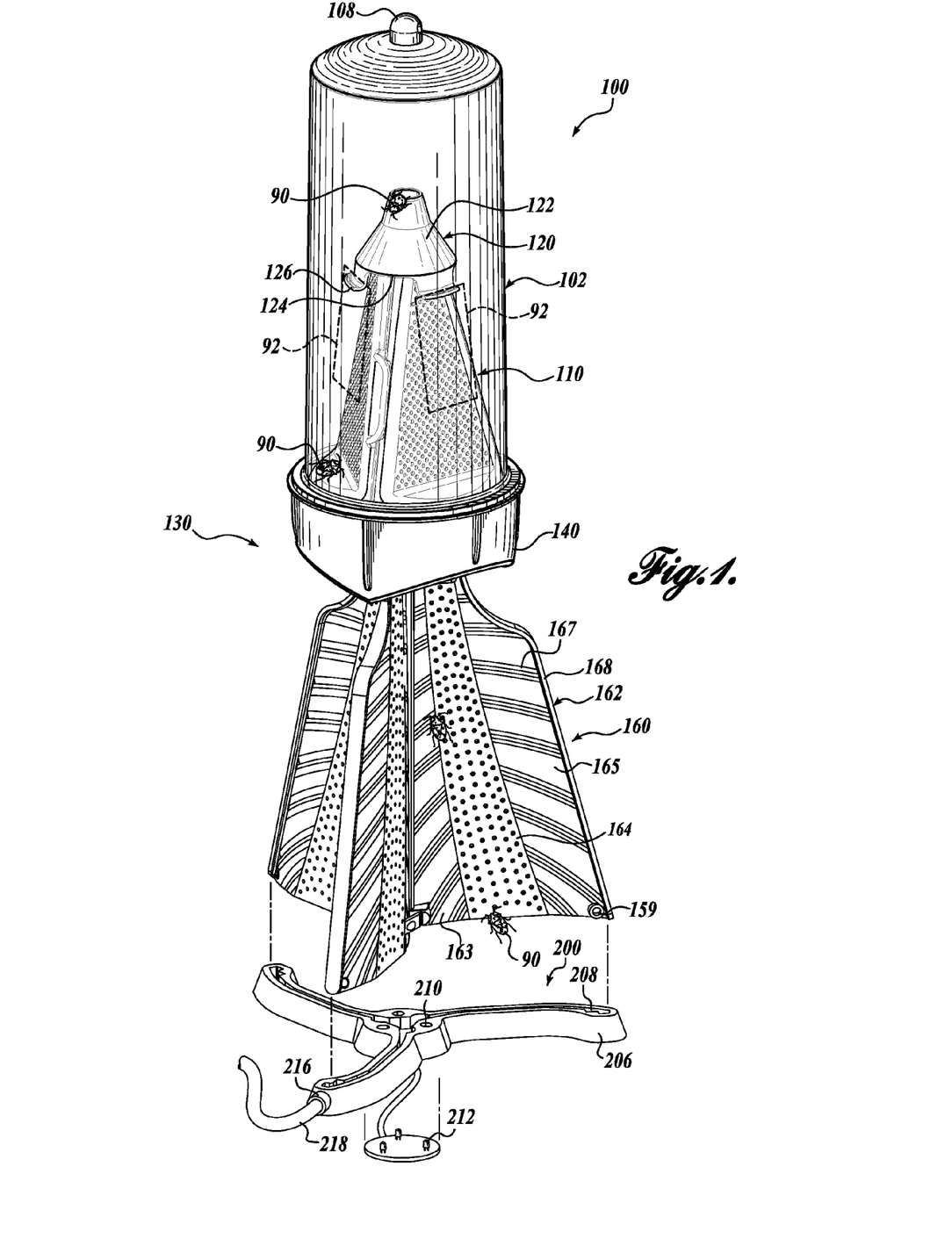
FIG. 1 is a perspective view of an exemplary stink bug trap, which may be employed with or without the pictured illumination accessory, that may comprise murgantiol.

A non-limiting example of a stink bug trap is shown in FIG. 1. FIG. 1 is a perspective view of an insect trap 100 in accordance with the present invention that is particularly suited for capturing insects such as stink bugs 90, for example, brown marmorated stink bugs and the like.

The trap 100 comprises an upper entrapment chamber 102, which in this embodiment is a generally cylindrical member that is open at a bottom end and closed at a top end. However, it will be readily apparent that the entrapment chamber may be alternatively shaped, without departing from the present invention. The top end may optionally include a nib 108 to facilitate securing the trap 100 at a desired location. The entrapment chamber 102 may be formed from a transparent or translucent material to permit light to enter the entrapment chamber. It is also contemplated that the color of the entrapment chamber 102 will preferably be selected to attract the target species.

An inner member herein referred to as the cone 110 is disposed in the entrapment chamber 102, tapering from a large opening at the bottom end disposed near the entrapment chamber bottom end, to a small opening at the top end disposed inside the entrapment chamber 102. A collar 120 is attached over a top end of the cone 110. The collar 120 in this embodiment includes a frustoconical upper portion 122 with a top edge that engages the cone 110 and a lower edge 124 that extends away from the cone 110. One or more hook members 126 extend down from the lower edge 124. Preferably the surface of the frustoconical upper portion 122 is provided with a slippery or non-stick surface to facilitate the target insects 90 falling too near the bottom of the entrapment chamber 102 and to prevent insects 90 from crawling back out of the trap 100. For example, the upper portion 122 may include a layer of polytetrafluoroethylene powder (e.g., with a particle size of 0.1 to 3.0 microns) such as that marketed under the trade names Teflon® or Fluon®.

A lower base portion 130 of the trap 100 includes an annular lid 140 that is releasably attached to the entrapment chamber 102, and a vane assembly 160 assembled from a plurality of panels or vanes 162 (three shown) that extend downwardly from the annular lid 140.

As illustrated in phantom in FIG. 1, one or more sources of attractant 92 are preferably enclosed within the entrapment chamber 102. The attractant disposed in the trap is typically packaged, formulated, or otherwise adapted to release gradually over time. Thus, in an exemplary embodiment the attractant 92 is containerized in a porous package or in a package that the user opens at the top, although other controlled release disposers or devices may alternatively be used. In the illustrated embodiment, each attractant package 92 is retained on one of the hook members 126 of the collar 120. The attractant may be murgantiol or a murgantiol-containing composition, as described herein. More generally, murgantiol may, for example, be disposed within the entrapment chamber 102, such as in a controlled release dispenser or device, between the cone 110 and the wall of the cylinder.

In the present embodiment the vanes 162 are designed with particular features that also take advantage of the stink bug's 90 behavioral tendencies. Stink bugs 90, for example, tend to alight on a surface, such as the ground, and to climb. For example, they may approach and even strike a vane 162 causing them to land at the base of the vane 162. The vanes 162 are designed to encourage the insect 90 to climb the vane 162 and to enter the entrapment chamber 102.

In this exemplary embodiment the vanes 162 are each curved in horizontal cross section to provide a more natural and organic shape that will be more inviting to the insect 90. For example, the vanes 162 may each be curved about a vertical axis. As seen most clearly in FIG. 1, the vanes 162 may include a center portion 164 that is substantially planar, an inner portion 163 extending inwardly from the center portion 164, and an outer portion 165 extending outwardly from the center portion 163, wherein the inner and outer portions 163, 165 are curved in horizontal cross section.

The vanes 162 are further provided with surface features that encourage and facilitate climbing. For example, in the present embodiment the center portions 164 are provided with a plurality of apertures that extend along the length of the vane 162. The apertures facilitate climbing by providing a perch for the insects 90, and also permit air and light to penetrate, again providing a more organic-mimicking environment to encourage continued climbing. The inner portion 163 and outer portion 165 of each vane 162 further include a plurality of surface ridges 167 that extend generally from the center portion 164 to the inner and outer edges of the vane 162. The ridges 167 generally mimic a leaf vein structure and further facilitate climbing the vane 162, and gently encourage the insects 90 toward the center portion 164. The outer edge of each vane 162 is further provided with a flange 168, such that climbing insects 90 are directed upwardly.

Optionally, the vanes 162 may further comprise means for fixing the trap 100 at a particular location. For example, apertures 159 in the lower outside corners of each vane 162 in the current embodiment may be provided with a string, cable, tie wrap, or the like (not shown) that can be secured to a fixed object, such as a portion of a tree, a pipe, etc.

LED lights may be incorporated into the trap of FIG. 1 by, for example, a cap comprising LED lights that fits on the top of the trap (see FIG. 2), or an illumination stand 200 suitable for use with insect traps such as the insect trap 100 may be employed. The illumination stand 200 in this embodiment comprises a unitary base member having a center portion and three outwardly extending arcuate arms 206. The base member defines a Y-shaped slot 208 extending along most of the length of all three arcuate arms 206. The Y-shaped slot 208 is sized and shaped to slidably receive and retain the vanes 162 of the trap 100.

The base member further includes three upwardly oriented apertures 210 in the center portion. The apertures 210 are sized and positioned to receive corresponding lighting elements, for example light emitting diodes 212. The light emitting diodes 212 may be conveniently mounted on a circuit board or the like. The base member may include a socket or jack 216 that is configured to receive power from an external source 218 to power the light emitting diodes 212. Conventional items such as a power switch, dimmer, and the like (not shown) are also contemplated. In a currently preferred embodiment, one or more of the arcuate arms 206 are configured to receive a power source, such as an AA or AAA battery, which may obviate the need for socket or jack 216 and external source 218.

The light emitting diodes 212 are preferably selected to emit light at a frequency or in a range of frequencies that are directed to attracting the particular insect 90 that is targeted by the trap 100. For example, it a current embodiment the light emitting diodes 212 emit light blue or near-blue portion of the spectrum, between 380 nm (violet) and 495 nm (cyan/green). It is believed that certain bugs, including stink bugs, are better attracted with light having wavelengths in this range. In a particular embodiment, the emitted light has a wavelength in the range of 450-475 nm. It is believed to be well within the skill and relatively straightforward to determine a preferred light color for a particular insect or species. It is contemplated that the apertures 210 may further include a lens, colored or transparent, (not shown) to obtain a desired light spread and color.

Figure 2:
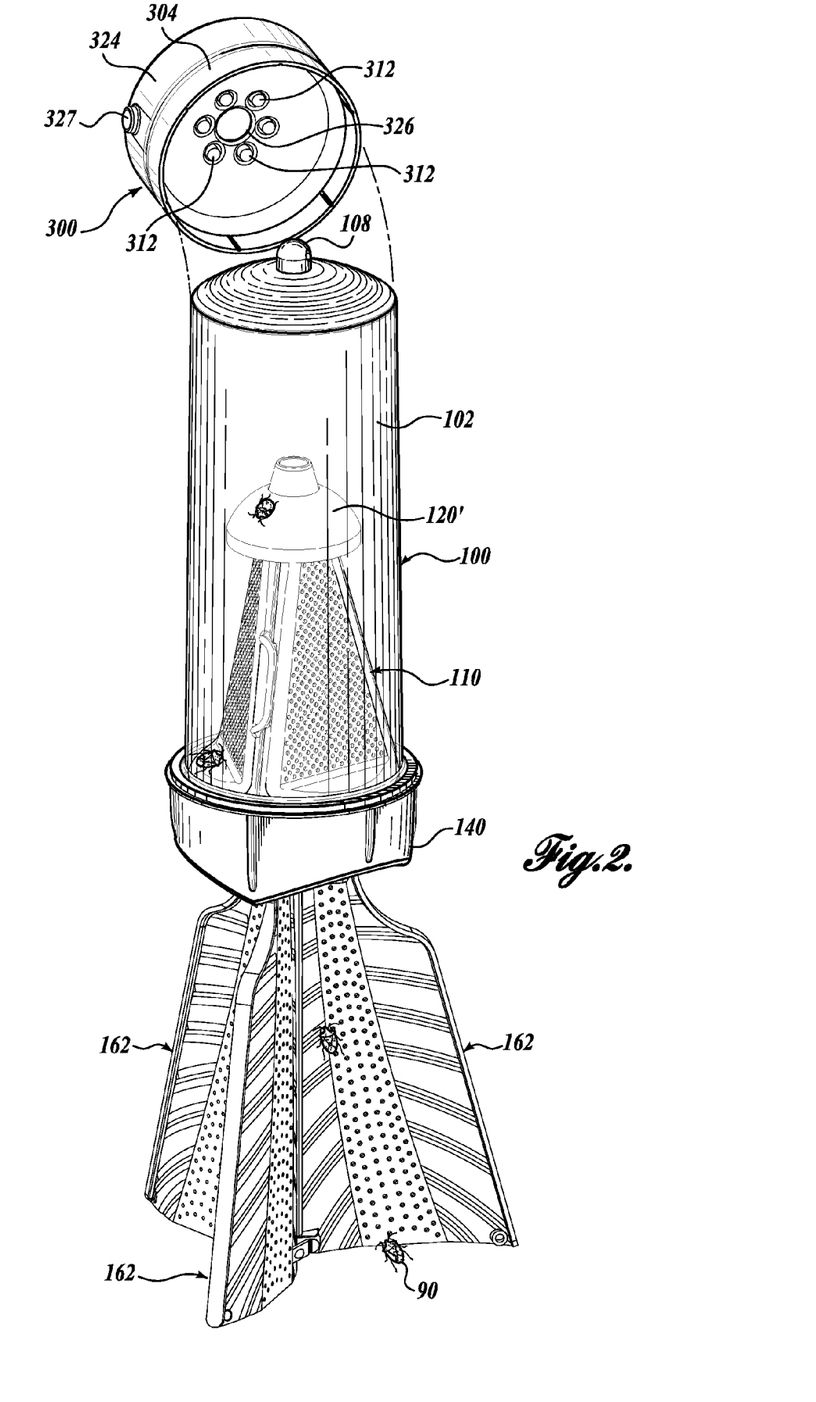
FIG. 2 shows another exemplary stink bug trap that may comprise murgantiol comprising a cap-type illumination assembly.

Another non-limiting example of a stink bug trap is shown in FIG. 2.

FIG. 2 shows insect trap 100 with a cap-type illumination assembly 300. The lights 312 in the illumination assembly 300 are directed downwardly, through the transparent top of the entrapment chamber 102, illuminating the interior of the trap 100. The light at least partially reflects off the entrapment chamber, cone 110, and collar 120' such that the interior of the trap 100 is well-illuminated. The cap-type illumination assembly is described further below. The cone 110 has an upper aperture and has a plurality of small apertures through the walls. Therefore, the cone 110 allows light transmission through the cone 110, and through the center aperture of the annular lid 140, thereby diffusely illuminating the vanes 162 below.

Therefore, insects 90 alighting on or near the vanes 162 will perceive the diffusely illuminated vanes 162, with progressively brighter lighting of the cone 110, leading the insects toward the entryways found between annular lid 140 and vanes 162. In some embodiments, the lighting from above provided by the cap-type illumination assembly 300 is more effective at attracting certain insects into the trap 100 than the base-mounted lighting described above. The improved effectiveness may be the result of the cap-type illumination assembly 300 providing lighting cues to such insects that more closely emulate natural lighting filtering through plant foliage and the like. The cap-type illumination assembly 300 pictured in FIG. 2 has a bowl-shaped lower portion that is sized and shaped to fit over an upper end of an associated insect trap, such as the insect trap 100 described above (FIG. 1). The illumination assembly 300 includes a light fixture having one or more lights (six shown), for example light emitting diodes 312 that are oriented downwardly, such that when energized the lights 312 emit light into the entrapment chamber 102. An aperture 327 in the upper segment 324 provides access to a socket. Although the illumination assembly 300 is currently configured to be powered externally, it will be appreciated that other means may be used, for example, internal batteries.

In the current embodiment the cap-type illumination assembly 300 is formed with a lower segment 304 shaped to fit over the entrapment chamber 102. An upper segment 324 is attached to the lower segment 304, for example with a snap fit, threaded attachment, or the like. The lower and upper segments 304, 324 cooperatively define and center aperture 326 therethrough; aperture 326 may accommodate nib 108 or a string, lanyard, or other attachment means (not shown) attached to entrapment chamber 102 may extend through the center aperture 326, for securing the trap 100 and illumination assembly 300 to an external support.

It is to be understood that traps of FIGS. 1 and 2 are only exemplary and not limiting, and that light emitting elements may be positioned in numerous places regarding the trap, without limitation.

It is contemplated that any embodiment discussed in this specification can be implemented with respect to any method, compound(s), or composition(s) of the invention, and vice versa. Furthermore, compounds and compositions of the invention can be used to achieve methods of the invention. Moreover, in any embodiment herein, one or more elements may be omitted.

The use of the term "or" in the claims is used to mean "and/or" unless explicitly indicated to refer to alternatives only or the alternatives are mutually exclusive, although the disclosure supports a definition that refers to only alternatives and "and/or."

The use of the word "a" or "an," when used in conjunction with the term "comprising" in the claims and/or the specification may mean "one," but it is also consistent with the meaning of "one or more," "at least one," and "one or more than one."

EXAMPLE

Indoor Behavioral Response of Brown Marmorated Stink Bugs to the Harlequin Bug Pheromone, Murgantiol A trapping experiment was carried out inside three homes with decent overwintering stink bug populations in Pittsburgh, Pa., during twelve days in early May to study potential attraction of the BMSB adults to a known Harlequin bug pheromone, murgantiol. During or before the experiment, overwintering stink bugs started waking up from their hibernation stage and walking/crawling inside homes. Three treatment lures and a blank control were tested using Sterling Rescue!® Stink Bug Traps (FIG. 1) in a block design. The three treatments included (i) 5 mg of more polar murgantiol mixture (a mixture of 8 more polar stereoisomers); (ii) 5 mg of less polar murgantiol mixture (a mixture of 8 less polar stereoisomers); and (iii) 5 mg of a racemic mixture of all 16 murgantiol stereoisomers. The test samples of (i), (ii), and (iii) were synthesized and separated based on the methods described by Zahn et al., *J. Chem. Ecol.* 34:238 (2008). The following scheme outlines the method starting from citronellal to prepare a racemic mixture of stereomers:

The more polar murgantiol mixture and the less polar murgantiol mixture were obtained and separated from the racemic mixture of murgantiol by flash chromatography on silica gel, eluting with 10% ethyl acetate in hexane, with the first fraction being the less polar mixture and the later eluting fraction being the more polar mixture. Each fraction consists of 8 isomers that are inseparable by the flash chromatography.

Lures were prepared by loading hexane solutions of the test compounds with 1% butylated hydroxytoluene (BHT) added as stabilizer onto grey rubber septa (5 mm sleeve-type; The West Co., Lititz, Pa.) via a rotor evaporator. The blank control dispensers were made in the same fashion as the treatment lures, but without any murgantiol mixtures—that is, rubber septum with hexane only. A set of four Sterling Rescue!® Stink Bug Traps baited with three different isomer mixture test samples of murgantiol dispensers and the blank control were set up in the same room of each selected home on the floor or hung from walls near windows (where stink bug activities were seen earlier). The starting positions of the four test traps within each set (room) were assigned randomly. The distance between traps within the same set was about 8-10 feet, depending on the size of each test room. Traps were checked every day and emptied when ≥5 bugs were captured in the best trap within the set, and their positions were re-randomized for a new replicate to minimize any positional effects.

Trap catch data were converted to proportion (P) of total captured bugs within each replicate to meet the assumptions of normality and homogeneity of variances for ANOVA (analysis of variance). Means were compared by ANOVA followed by the Duncan's multiple range test at α=0.05.

Figure 3:
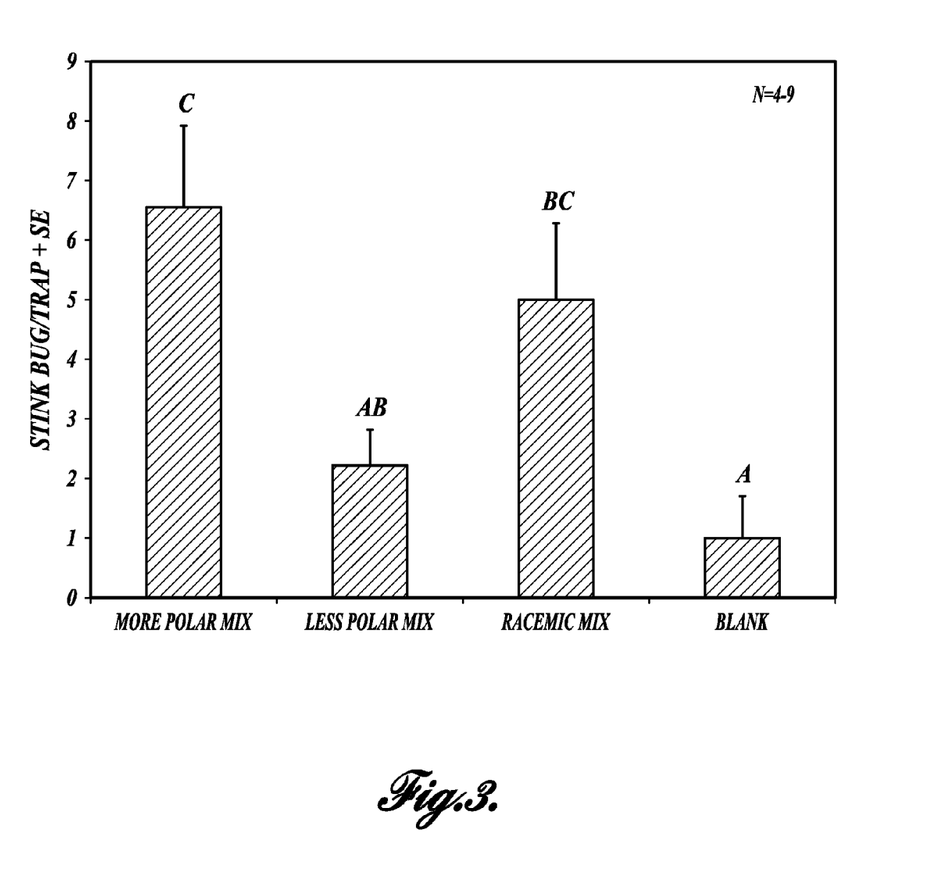
FIG. 3 illustrates behavioral attraction of the indoor brown marmorated stink bug, Halyomorpha halys (Stål), to traps baited with different mixtures of murgantiol stereoisomers, plus a blank control during the overwintering period indoors (bars with the same letter are not significantly different ($P>0.05$) by Duncan's multiple range test after ANOVA).

As shown in FIG. 3, the blank control traps caught an average of 1 bug/trap, which was not significantly different from zero [95% confidence interval (CI) includes 0: −1.25 to 3.25]. Traps baited with the less polar murgantiol mixture were weakly attractive compared to the blank control, but were significantly different from zero [95% confidence interval (CI) does not include 0: 0.85 to 3.6]. Traps baited with the more polar murgantiol mixture showed strong attraction to the stink bugs and caught six times as many stink bugs as the blank control traps. Traps baited with the racemic mixture of all 16 murgantiol stereoisomers also showed significant attraction to the indoor stink bugs and captured five times as many stink bugs as the blank control traps.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for attracting a brown marmorated stink bug, comprising placing a composition comprising murgantiol into a trap configured to attract and trap a brown marmorated stink bug, and attracting the brown marmorated stink bug into the trap.

2. The method of claim 1, wherein the trap further comprises a plurality of lighting elements.

3. The method of claim 2, wherein the lighting elements comprise light emitting diodes.

4. The method of claim 1, wherein the device that controllably releases the composition.

5. The method of claim 1, wherein the composition further comprises methyl (2E,4E,6Z)-decatrienoate, methyl (2E,4Z)-decadienoate, ethyl (2E,4Z)-decadienoate, methyl (2Z,4E)-decadienoate, methyl (2E,4E)-decadienoate, related stereoisomers thereof, or a combination thereof.

6. The method of claim 1, wherein the composition further comprises an antioxidant.

7. The method of claim 1, wherein the composition further comprises an oil.

8. A method of attracting a brown marmorated stink bug to a trap, comprising placing a composition comprising murgantiol into a trap configured to attract and trap a brown marmorated stink bug; and attracting the brown marmorated stink bug into the trap, wherein the trap comprises a plurality of lighting elements.

9. The method of claim 8, wherein the lighting elements comprise light emitting diodes.

10. The method of claim 1, further comprising placing the trap in an indoor location and attracting the brown marmorated stink bug to the trap in the indoor location.

11. The method of claim 8, further comprising placing the trap in an indoor location and attracting the brown marmorated stink bug to the trap in the indoor location.

12. The method of claim 8, wherein the composition further comprises methyl (2E,4E,6Z)-decatrienoate, methyl (2E,4Z)-decadienoate, ethyl (2E,4Z)- decadienoate, methyl (2Z,4E)-decadienoate, methyl (2E,4E)-decadienoate, related stereoisomers thereof, or a combination thereof.

* * * * *